United States Patent
Son

(10) Patent No.: US 10,183,063 B2
(45) Date of Patent: Jan. 22, 2019

(54) INJECTION COMPOSITION COMPRISING HYALURONIDASE FOR REMOVAL OF TOPICAL FAT

(71) Applicant: Youna Son, Seoul (KR)

(72) Inventor: Youna Son, Seoul (KR)

( * ) Notice: Subject to any disclaimer, the term of this patent is extended or adjusted under 35 U.S.C. 154(b) by 0 days.

(21) Appl. No.: 15/658,703

(22) Filed: Jul. 25, 2017

(65) Prior Publication Data

US 2018/0071372 A1 Mar. 15, 2018

(30) Foreign Application Priority Data

Sep. 9, 2016 (KR) ........................ 10-2016-0116462

(51) Int. Cl.

| | | |
|---|---|---|
| *A61K 38/47* | (2006.01) | |
| *A61K 8/20* | (2006.01) | |
| *A61K 8/41* | (2006.01) | |
| *A61K 8/42* | (2006.01) | |
| *A61K 8/44* | (2006.01) | |
| *A61K 8/49* | (2006.01) | |
| *A61K 8/66* | (2006.01) | |
| *A61K 8/67* | (2006.01) | |
| *A61K 9/00* | (2006.01) | |
| *A61K 9/08* | (2006.01) | |
| *A61K 47/02* | (2006.01) | |
| *A61Q 19/06* | (2006.01) | |
| *A61K 31/167* | (2006.01) | |
| *A61K 31/195* | (2006.01) | |
| *A61K 31/375* | (2006.01) | |
| *A61K 31/4402* | (2006.01) | |

(52) U.S. Cl.
CPC ................ *A61K 38/47* (2013.01); *A61K 8/20* (2013.01); *A61K 8/41* (2013.01); *A61K 8/42* (2013.01); *A61K 8/44* (2013.01); *A61K 8/4926* (2013.01); *A61K 8/66* (2013.01); *A61K 8/676* (2013.01); *A61K 9/0019* (2013.01); *A61K 9/08* (2013.01); *A61K 31/167* (2013.01); *A61K 31/195* (2013.01); *A61K 31/375* (2013.01); *A61K 31/4402* (2013.01); *A61K 47/02* (2013.01); *A61Q 19/06* (2013.01); *C12Y 302/01035* (2013.01); *A61K 2800/782* (2013.01); *A61K 2800/91* (2013.01)

(58) Field of Classification Search
None
See application file for complete search history.

(56) References Cited

U.S. PATENT DOCUMENTS

2013/0210760 A1* 8/2013 Liu et al.

FOREIGN PATENT DOCUMENTS

| KR | 10-07710580000 B1 | 10/2007 |
| KR | 10-2009-0111916 A1 | 10/2009 |
| KR | 10-2013-0000988 A1 | 1/2013 |
| KR | 10-2014-0146074 A | 12/2014 |
| KR | 10-15062040000 B1 | 3/2015 |

OTHER PUBLICATIONS

Sivagnanam, G., J Pharmacol Pharmacother, 2010, vol. 1, No. 1, p. 4-8.*
Kim et al., Korean J Anesthesiol., 2011, vol. 60, No. 1, p. 57-59.*
Almeida et al., Surg Cosmet Dermato, 2015, vol. 7, No. 3, p. 197-204.*
Mesotherapy Protocols, Mesotherapy Worldwide, 2005, pp. 27-28.*
PCT International Search Report dated Nov. 2, 2017 in connection with PCT International Patent Application No. PCT/KR2017/007821, 3 pages.
Ji E et al., entitled "Inhibition of Adipogenesis in 3T3-L1 cells and suppression of abdominal fat accumulation in high-fat diet-feeding C57BI/6J mice after downregulation of hyaluronic acid," International Journal of Obesity (2014) 38, 1035-1043.
KIPO Notification of Reason for Refusal dated Dec. 1, 2016 in connection with Korean Patent Application No. 10-2016-0116462.
Written Opinion dated Dec. 1, 2016 in connection with Korean Application No. 10-2016-0116462.

* cited by examiner

*Primary Examiner* — Kade Ariani
(74) *Attorney, Agent, or Firm* — Amster, Rothstein & Ebenstein LLP

(57) ABSTRACT

The present invention relates to an injection composition comprising hyaluronidase for topical fat reduction. More particularly, the present invention relates to an injection composition comprising 300 IU to 600 IU of hyaluronidase and a local anesthetic, an antihistamine, a lipolysis stimulator and a collagen production stimulator. The present invention promotes the reduction of topical fat tissue, thereby improving obesity and helping weight loss and maintenance of body shape while preventing side effects or skin imbalance by the even removal of fat. Further, at the same time, the present invention can achieve a skin lifting effect where skin resilience is maintained by the stimulation of collagen production.

2 Claims, No Drawings

INJECTION COMPOSITION COMPRISING HYALURONIDASE FOR REMOVAL OF TOPICAL FAT

CROSS-REFERENCE TO RELATED APPLICATIONS

The present application claims priority from Korean Patent Applications No. 10-2016-0116462 filed on Sep. 9, 2016, the entire subject matter of which is incorporated herein by reference.

TECHNICAL FIELD

The present invention relates to an injection composition comprising hyaluronidase for the removal of topical fat. More specifically, the present invention relates to an injection composition comprising 300 IU to 600 IU of hyaluronidase and one or more local anesthetics, antihistamines, lipolysis stimulators and collagen production stimulators. Further, the present invention relates to a method for a reduction of topical fat by injecting an injection composition comprising 300 IU to 600 IU of hyaluronidase and one or more local anesthetics, antihistamines, lipolysis stimulators and collagen production stimulators.

The present invention stimulates the reduction of topical fat tissue, thereby improving obesity and helping weight loss and the maintenance of body shape, while preventing side effects due to the use of drugs or skin imbalance by the even removal of fat and achieving a skin lifting effect where skin resilience is maintained by stimulation of collagen production.

BACKGROUND

With the recent increase in obese population, obesity is gaining more attention and the number of obesity clinics is growing, and various social problems arising from obesity are becoming an issue.

Simply speaking, obesity is defined as an over-accumulation of body fat and causes adult diseases such as hypertension, diabetes, and hyperlipidemia, constituting a major part of metabolic syndrome.

Particularly, women tend to desire a slimmer and more balanced body line even when they are not obese.

In order to remove topical fat such as abdominal fat, etc. accumulated from such obesity, a surgical procedure called liposuction is widely used.

However, such surgical procedure may cause severe side effects, such as wounds at the operated sites, edema, paralysis and burning sensation, risk of infection, other injuries to skin or nerves, or perforation of vital organs.

In addition, liposuction requires a substantial amount of recovery time, and there are always serious anesthesia-related risks since surgical procedures like liposuction require local anesthesia or general anesthesia depending on the case.

For the reasons explained above, various lipolysis stimulators which break down topical fat have been used recently to improve external obesity resulting from the accumulation of body fat.

Lipolysis refers to the process in which triglycerides are hydrolyzed into free fatty acids (FFA) and glycerol by the action of hormone sensitive lipase (HSL) accumulated in adipocytes.

The lipolytic agent hyaluronidase, which is the collective name for enzymes catalyzing the degradation of hyaluronic acid, was first known as a dispersion component by Duran-Reynals, but, as it was later observed to exhibit strong activity on hyaluronic acid (HA), it came to be called hyaluronidase (HAase).

Hyaluronidase is known to hydrolyze the linkage between N-acetyl-D-glucosamine and D-glucuronic acid present in hyaluronic acid (HA), chondroitin, and chondroitin sulfates.

Hyaluronidase can accumulate in the dermis and depolymerize long chain mucopolysaccharides causing the retention of associated water and the delay of organic fluid diffusion removing metabolic waste products by microvascular constriction.

Depolymerization of mucopolysaccharides cleaves their long chains into short chains, resulting in the loss of associated water and waste products as well as recovery of venous and lymphatic circulation, thereby achieving the dissipation of localized edema. Utilizing such connective tissue lysing action, hyaluronidase is used in methods of topical fat removal by injecting it subcutaneously to loosen abdominal connective tissue, thereby reducing edema in the tissue and consequently helping blood and lymph circulations so that the degradation and metabolism of abdominal adipose cells are facilitated.

Among the above methods of topical fat removal by lipolysis using hyaluronidase, LLD (Lipolytic Lymph Drainage) treatment is widely used (KR 10-2009-0111916A).

LLD treatment destroys some adipose cells and causes the accumulated fat-related substances to rapidly move to the lymph vessel and be oxidized and excreted, consequently reshaping the overall body line.

However, in the above document, a high dose (1500 IU) hyaluronidase was used, in which case it is difficult to remove fat evenly over a wide area, resulting in dimpling, sagging and wrinkles in the skin. Also, the side effects of the drug make continuous treatment difficult.

In addition, KR 10-2013-0003394A discloses an injection composition preventing pain and allergy by mixing 1 cc each of hyaluronidase, lidocaine which is a local anesthetics, and pheniramine which is an antihistamine. However, this composition also uses hyaluronidase at a high dose, and injection of the composition is performed on 4 to 6 points with a 5-cm interval between the injection points, and thus still has the problem of not being able to avoid the side effects such as dimpling or sagging and wrinkling.

SUMMARY

It is an object of the present invention to provide an injection composition for topical fat removal which can minimize side effects such as dimpling or sagging and wrinkling by removing fat evenly over a wide area, minimizing the side effects of injection compositions used in LLD treatment to resolve the above-mentioned problems.

Further, it is an object of the present invention to provide an optimal injection composition which can stimulate collagen production so that skin resilience is maintained in the local area where fat was removed.

The present invention was completed by discovering an optimal unit dose of hyaluronidase and combination of additives and their compositional ratios as a result of a long period of clinical trials to enhance lipolysis and minimize the side effects of hyaluronidase-containing injection compositions for LLD treatment.

That is, in order to inhibit dimpling, sagging and wrinkling, which are side effects due to excessive lipolysis by high dose hyaluronidase injections, and the occurrence of reduced skin resilience and bruising from subcutaneous bleeding and edema, an optimal unit dose of hyaluronidase has been found, and it has been possible to prepare an injection composition by adding an antihistamine to prevent allergy, a local anesthetic to alleviate injection pain, a lipolysis stimulator for rapid degradation of fat, and a collagen stimulator for recovering skin resilience following lipolysis.

Hyaluronidase is an enzyme that is capable of hydrolyzing mucopolysaccharides in the form of hyaluronic acid. It is produced in the testis of mammals and is made available in a white or yellowish white powder with the addition of a suitable stabilizer.

With conventional hyaluronidase injections, it is impossible to carry out continued treatment due to concerns about potential side effects because they use a high dose of 1500 IU (International Unit, mg) (KR 10-2009-0111916A). Furthermore, since it is difficult to administer hyaluronidase at a daily dose exceeding 15,000 IU, it cannot be injected at narrow intervals over a wide area such as the abdomen. Consequently, it was difficult to remove fat evenly, resulting in the occurrence of dimpling or wrinkles and sagging at the site of fat removal.

In order to find the optimal doses of hyaluronidase facilitating lipolysis, the present inventor conducted experiments with hyaluronidase unit doses of 10 IU, 50 IU, 100 IU, 150 IU, 200 IU, 250 IU, 300 IU, 350 IU, 400 IU, 450 IU, 500 IU, 550 IU, 600 IU, 650 IU, 700 IU, 750 IU, 800 IU, 850 IU, 900 IU, 950 IU, 1000 IU, 1050 IU, 1100 IU, 1150 IU, 1200 IU, 1250 IU, 1300 IU, 1350 IU, 1400 IU, 1450 IU, and 1500 IU. The results showed that at 300 IU or below, while it was possible to dissolve fillers, sufficient lipolysis did not occur. At above 600 IU, while excellent effects were obtained in terms of fat removal, side effects were observed which was the problem with conventional injection compositions where skin became bumpy due to dimpling resulting from excessive lipolysis. The present invention was completed upon ascertaining through clinical trials that at the hyaluronidase unit dose of 300 IU to 600 IU, it was possible to ensure the fat removal effect while minimizing side effects.

It was shown in clinical trials that at the above dose range, if the injection composition is administered in a volume of 1 cc containing 300 IU of hyaluronidase, the diameter of the diffusion range is about 1 cm. Thus, with the hyaluronidase dose set at 300 IU to 600 IU, by injecting the composition at a volume of 0.5 to 2 cc depending on the hyaluronidase dose and at injection points with an interval of 0.5 to 1.5 cm between the injection points, injection at narrow intervals is possible and consequently, lipolysis occurs evenly. Furthermore, a lifting effect occurs concomitantly where skin resilience is improved by the promotion of collagen production through stimulation of the skin by the injection needle.

In addition, the present invention provides an injection composition which further comprises a local anesthetic to alleviate the pain from injection, an antihistamine to prevent allergy, a lipolysis stimulator to promote lipolysis, and a collagen stimulator.

More specifically, the injection composition of the present invention comprises, based on a volume of 1 cc, 300 IU to 600 IU of hyaluronidase, 0.80 to 4.00 mg of a local anesthetic, 0.10 to 0.20 mg of an antihistamine, 0.1 to 40 mg of a lipolysis stimulator, and 1 to 20 mg of a collagen stimulator, with the remainder being a saline solution.

The above amounts were determined in consideration of the fact that the daily dose is 15,000 IU for hyaluronidase, 200 mg for local anesthetics, 10 mg for antihistamine, 2000 mg for lipolysis stimulator, and 1000 mg for collagen production stimulator. Amounts exceeding the above ranges may cause side effects.

While lidocaine and procaine can be used as the above local anesthetics, the time until the onset of action for the local anesthetic effect of procaine is more than 10 minutes later when compared to lidocaine. Moreover, since it was found that lidocaine has a higher lipid solubility, protein binding, and more effective anesthetic effect compared to procaine, lidocaine was selected.

Local anesthetics should be used in minimal amounts as they may exhibit toxicity when used in excessive amounts. Clinical trials showed that the most preferable dose is 0.80 to 4.00 mg per 1 cc of injection agent. At a dose below the above value, anesthetic effect is unsatisfactory and at a dose above the above value, patients experience inconveniences in daily life as it takes more than 2 hours to fully recover sensation after injection and the probability of side effects due to lidocaine increases.

As the antihistamine of the present invention, first generation antihistamines were selected since the antihistamine should exhibit an immediate effect during the injection. Among them, those that can be administered subcutaneously include piprinhydrinate (=diphenylpyridine) and pheniramine or its analogue, chlorpheniramine, with chlorpheniramine found to be more preferable, having less side effects and a shorter duration of action.

The amount of the antihistamine used is 0.10 to 0.20 mg per 1 cc. At a dose below the above value, antihistamine effect is unsatisfactory and above it, side effects due to antihistamine may occur.

As the lipolysis stimulator of the present invention, L-carnitine is used. L-carnitine is a type of vitamin and a nutrient essential for energy production and fat oxidation. In adults, it is synthesized in the liver and kidney and taken from animal source food or dietary supplements.

L-carnitine is an essential substance for the transportation of fatty acids across the mitochondrial membrane and β-oxidation, and carnitine palmitoyltransferases I and II and acylcarnitine translocase are involved in the action of L-carnitine.

Recent research shows that carnitine palmitoyltransferase I is an important rate-limiting enzyme in the fat oxidation and plays a key role in the utilization as substrate for energy production.

L-carnitine is also a modulator of glucocorticoid receptor functions and plays a role similar to a glucocorticoid, stimulating lipolysis in the adipose tissue.

As the lipolysis stimulator, L-carnitine can be used. Although L-carnitine is produced in the body, the amount is not sufficient and consequently, it needs to be supplied from outside. Since L-carnitine is mostly present in animal proteins, a strict vegetarian diet may lead to carnitine deficiency.

Thus, while L-carnitine is essential to facilitate the degradation of body fat and increase metabolism to improve obesity, it can be easily deficient if not supplied from outside.

In particular, when one cuts back on the intake of animal proteins during a period of diet, L-carnitine almost inevitably becomes deficient, with the rate of fat burning reduced as well as the metabolism rate. Therefore, in order to enhance the effect of diet and improve metabolic diseases, the addition of L-carnitine is thought to be necessary.

However, L-carnitine can cause side effects such as nausea, vomiting, upset stomach, diarrhea, and body odor, and can also cause seizures and increase the frequency and intensity of seizures in patients with a history of seizures. As a result of numerous studies to find the doses that promote the metabolism of fat while minimizing the above side effects, it has been found that L-carnitine can be administered in an amount of 0.1 to 40 mg per 1 cc of injection composition.

In addition, using L-carnitine together with a lipolytic agent such as phosphatidylcholine, aminophylline, caffeine, or the like can further improve the lipolytic effect.

Furthermore, in order to prevent skin sagging which is the biggest problem in lipolysis and diet and make a resilient and beautiful body line, non-toxic vitamin C was selected as a collagen production substance.

Vitamin C has the effect of increasing the resilience of skin by collagen production, and is a natural antihistamine. Thus, it was necessary to find the minimal effective dose to prevent side effects associated with administration of excess amount. Clinical trials showed that 1 to 20 mg of vitamin C per 1 cc of injection composition is most preferable.

The injection composition of the present invention may further comprise, without limitation, placenta components that are excellent in skin regeneration and anti-aging or pentoxifylline which improves blood circulation, within dose ranges allowable for injection compositions.

The injection composition as described above is useful in that it has an excellent effect in topical fat removal as it allows narrow interval injection and minimizes side effects to enable continued treatment, prevention of dimpling by even fat removal and maintaining skin resilience by collagen production.

In addition, the present invention provides a method for a reduction of topical fat by injecting the injection composition comprising 300 IU to 600 IU of hyaluronidase and one or more local anesthetics, antihistamines, lipolysis stimulators and collagen production stimulators. The said injection composition, hyaluronidase, local anesthetics, antihistamines, lipolysis stimulators and collagen production stimulators are same as explained above.

In the present invention, the injection composition is injected to give 300 IU to 600 IU of hyaluronidase per injection, at a unit volume of 0.5 to 2 cc with an interval between injection points of 0.5 to 1.5 cm. The daily dose of hyaluronidase is preferably 15,000 IU or less, and the unit dose and injection points can be suitably adjusted according to the unit of hyaluronidase given in one injection.

The injection composition of the present invention can be injected 10 to 50 times based on a volume of 1 cc containing 300 IU of hyaluronidase, and the site of injection can be any body area where fat is accumulated including abdomen, buttocks, thighs, calves, chin, forehead, arms, and the like.

The injection composition of the present invention minimizes side effects to allow continued obesity treatment, and enables slim and smooth skin regeneration without dimpling by even fat removal.

By collagen regeneration, the present invention also prevents skin sagging or wrinkling due to fat removal, thereby achieving skin lifting effect allowing skin resilience to be maintained.

DETAILED DESCRIPTION

The present invention will now be described in detail with reference to specific working examples.

Hyaluronidase is a water-soluble enzyme secreted from mammalian vas deferens or testes, characterized by its actions to remove barriers between tissues by hydrolyzing the glucosaminic bonds between hyaluronic acid, a major intercellular substance, and connective tissues to dissolve the bonds and reduce fibroplasia in tissues. Hyaluronidase is also known to relieve swelling and edema in tissues.

Using the characteristics of hyaluronidase that hydrolyzes and dissolves substances within skin tissues, LLD (Lipolytic Lymph Drainage) treatment is widely used in which hyaluronidase is directly injected subcutaneously to degrade substances including fibers in subcutaneous tissues, thereby facilitating lymphatic circulation to help drainage of adipose tissue to reduce adipose tissue and relieve obesity.

However, the above treatment, though helpful in reducing adipose tissue, has been associated with various side effects.

That is, using high doses of hyaluronidase to remove adipose tissue causes allergic symptoms such as redness or itching, and excessive lysis of adipose tissue leads to bruising due to subcutaneous bleeding or dimpling, resulting in frequent discontinuation of the LLD treatment to take care of these side effects and difficulty of continued treatment due to patients' repulsion arising from pain.

Furthermore, using high doses of hyaluronidase makes it difficult to narrow the interval between injection points (about 5-cm interval). As a result, fat removal is concentrated only around injection points to cause indentations or sagging and wrinkling in the skin, and these side effects lead to imbalance. Significant reduction in skin resilience also resulted in the dissatisfaction of patients.

Having strived to address the above problem, the present inventor discovered that the minimum amount of hyaluronidase exhibiting efficacy is 300 IU and that above 600 IU, adipose cells are excessively hydrolyzed, giving rise to concerns about dimpling or subcutaneous bleeding. Thus, by administering an injection composition of the present invention having the above compositional ranges, the side effects from using the drugs are minimized and fat removal over a wide area can be carried out using a minimal volume.

It was shown in clinical trials that at a hyaluronidase of 300 IU, the diameter of the diffusion range for the injection composition is about 1 cm. Thus, by injecting the composition at narrow intervals between injection points of 0.5 to 2 cm, even fat removal as well as collagen production by skin stimulation can be facilitated.

By comprising a local anesthetic to alleviate the pain from injection, an antihistamine to prevent allergic side effects, a lipolysis stimulator to rapidly transport fatty acids from degraded fat into mitochondria and degrade them, and a collagen stimulator, the injection composition of the present invention also prevents allergic symptoms like redness or itching as well as pain and bruising, accelerates fat removal, and excels in maintaining skin resilience by collagen production.

body area where fat is accumulated including abdomen, buttocks, thighs, calves, chin, forehead, arms, and the like.

EXAMPLES

Preparation of Injection Compositions

| Ingredients | Example 1 | Example 2 | Example 3 | Example 4 | Comp. Example 1 | Comp. Example 2 | Comp. Example 3 |
|---|---|---|---|---|---|---|---|
| Hyaluronidase | 30,000 IU | 30,000 IU | 60,000 IU | 30,000 IU | 25,000 IU | 65,000 IU | |
| Lidocaine | | 210 mg | 210 mg | 210 mg | 210 mg | 210 mg | |
| Peniramin | | 12 mg | 12 mg | 12 mg | 12 mg | 12 mg | |
| L-Carnitine | | | 660 mg | 660 mg | 660 mg | 660 mg | |
| Vitamin C | | | | 600 mg | 600 mg | 600 mg | |
| Saline solution | q.s. | q.s. | q.s. | q.s. | q.s. | q.s. | 100 |
| Total Amount (cc) | 100 | 100 | 100 | 100 | 100 | 100 | 100 |

As the above local anesthetic, drugs commonly used in injectable solutions can be used. The present invention uses lidocaine in an amount of 0.08 to 0.4% by weight based on the total weight of the composition.

When the amount of the local anesthetic is below 0.08%, analgesic effect is unsatisfactory, and when the amount is above 0.4%, the duration of anesthesia is prolonged and is uneconomical.

As for the other ingredients, the antihistamine pheniramin is contained in an amount of 0.01 to 0.02% by weight, the lipolysis stimulator L-carnitine in an amount of 0.01 to 4.0% by weight, and the collagen stimulator vitamin C in an amount of 0.1 to 2.0% by weight.

The composition of the present invention may also comprise one or more substances selected from a tonicity agent, a nonionic surfactant, a stabilizer, a preservative, etc. that are commonly used in injectable solutions, within dose ranges allowable for injection compositions. The composition of the present invention may further comprise a lipolytic agent such as phosphatidylcholine, aminophylline, caffeine, or the like as well as placenta components or pentoxifylline which improves blood circulation, in amounts of 0.01 to 4.0% by weight.

The amounts of the above ingredients were determined within their respective maximum daily doses in preparation for a case where 300 IU of hyaluronidase is administered at a daily dose of 15,000 IU.

Most preferably, the injection composition of the present invention is injected to give 300 IU to 600 IU of hyaluronidase per injection, at a unit volume of 0.5 to 2 cc with an interval between injection points of 0.5 to 1.5 cm. The daily dose of hyaluronidase is preferably 15,000 IU or less, and the unit dose and injection points can be suitably adjusted according to the unit of hyaluronidase given in one injection.

The injection composition of the present invention can be injected 50 times based on a volume of 1 cc containing 300 IU of hyaluronidase, and the site of injection can be any For hyaluronidase, Liporase Inj. of Daehan New Pharm Co., Ltd (1500 IU/vial, including 13.3 mg lactose hydrate) was used, to which lidocaine (Hanmi Pharm. Co., Ltd.), Peniramin (Yuhan Co.), L-carnitine (Dream Pharma) and vitamin-C (Daewoo Pharm Co., Ltd.) were added in the amounts listed in the above table, and the mixture was dissolved in saline solution to prepare 100 cc of a solution composition for injection.

Experimental Example 1

Lipolytic Effect of the Injection Composition of the Present Invention

Changes in waist circumference after the administration of the injection composition of Example 4 and those of Comparative Examples 1 to 3, as well as after endomology treatment for edema were measured and presented in Table 1.

The subjects of treatment were a total of 40 patients (20 male, 20 female) having abdominal obesity with a BMI of 25 or greater, selected from adult outpatients of age 20 or above.

In the abdominal area between the ribs and pubic bones, 1 cc each of an injection composition was injected at 50 points, arranged in a manner that they are apart 1 cm each starting from the navel. The above injection was repeated weekly for four weeks, with the points of injection moved each time. Decreases in waist circumference were measured 1 week after completion of the treatment, and then again 1 month after completion of the treatment. The average values of the measurements are presented in Table 1.

Endomology treatment, designed for edema, was carried out for four weeks, one 30-minute session per week, with the decrease in waist circumference measured after one week and one month, and the results are shown in Table 1.

For statistical analysis, the statistics package SPSS was used to obtain the distribution of measurements and the paired t-test was used to assess the effects of test injections on the decrease in waist circumference. The analysis used a 95% confidence interval, adjusted for weight changes.

TABLE 1

|  | Baseline | 1 week after 4 sessions | Difference after 1 week | 1 month after 4 sessions | Difference after 1 month |
|---|---|---|---|---|---|
| Comp. Example 3 | 90.7 ± 1.2 | 91.0 ± 1.8 | +0.3 ± 1.2 | 90.5 ± 1.3 | −0.2 ± 1.2 |
| Comp. Example 1 | 91.0 ± 1.0 | 89.4 ± 0.4 | −1.6 ± 0.6 | 89.8 ± 1.3 | −1.2 ± 0.3 |
| Comp. Example 2 | 90.7 ± 1.3 | — | — | — | — |
| Example 4 | 90.8 ± 1.7 | 81.4 ± 0.5 | −9.4 ± 0.2 | 81.3 ± 0.3 | −9.5 ± 0.4 |
| Endomology | 92.0 ± 2.0 | 89.8 ± 1.4 | −2.2 ± 0.8 | 92.2 ± 1.2 | +0.2 ± 1.5 |

※Example 4, body fat analysis using the body fat analyzer Inbody showed an average fat loss of 1.5 to 2 kg.

According to Table 1, a change of −0.2±1.2 cm in waist circumference was observed in Comparative Example 3, where only saline solution was given. In Example 4 according to the present invention, however, a difference of −9.4±0.2 cm in waist circumference was seen at one week after the four sessions, and the difference was maintained as −9.5±0.4 cm at one month after the four sessions, indicating that there was no yo-yo effect.

On the other hand, in Comparative Example 1 where 250 IU of hyaluronidase was administered, the difference was −1.6±0.6 cm at one week after the treatment and −1.2±0.3 cm at one month after the treatment, showing a significantly lower effect than the present invention. In Comparative Example 2 where 650 IU of hyaluronidase was administered, the treatment was discontinued after the first session due to dimpling and bruising.

In the case of endomology, a decrease in waist circumference from the removal of edema was not significant and disappeared after one month, clearly indicating that a decrease in waist circumference obtained by using hyaluronidase is not only a result of edema removal but also from lipolysis.

As can be seen from the above results, the injection composition of the present invention has been demonstrated to have an excellent effect in topical fat removal, with remarkably reduced side effects and no yo-yo effect.

In addition, the injection composition of the present invention has also been shown to have minimized side effects and improved topical fat removal effect despite the use of a lower dose of hyaluronidase compared to the high dose hyaluronidase injection composition of the prior art KR 10-2009-0111916A.

Experimental Example 2

Assessment of side effects of the injection composition of the present invention.

The injection compositions of Examples 1 to 4 and those of Comparative Examples 1 to 3 were administered as in Experimental Example 1, and the side effects observed in each patient in clinical trials are indicated in Table 2.

TABLE 2

|  | Redness | Swelling | Itching | Pain above VAS 3 | Bruising | Dimpling | Sagging | Skin resilience |
|---|---|---|---|---|---|---|---|---|
| Comp. Example 1 | 1 | 1 | 0 | 0 | 0 | 0 | 0 | 3 |
| Comp. Example 2 | 4 | 3 | 4 | 2 | 10 | 15 | 0 | 2 |
| Comp. Example 3 | 0 | 0 | 0 | 0 | 0 | 0 | 0 | 3 |
| Example 1 | 11 | 10 | 11 | 13 | 1 | 0 | 1 | 3 |
| Example 2 | 1 | 0 | 1 | 0 | 0 | 0 | 1 | 3 |
| Example 3 | 1 | 1 | 0 | 0 | 0 | 1 | 1 | 3 |
| Example 4 | 1 | 0 | 0 | 0 | 0 | 0 | 0 | 5 |

*Skin resilience was determined by tactile assessment using a 5-point scale: 1: Very poor, 2: Poor, 3: Fair, 4: Good, 5: Very Good.

As shown in Table 2, with the injection composition of Example 1 according to the present invention, which does not contain local anesthetics or antihistamines, side effects such as bruising or dimpling were remarkably reduced compared to the high dose composition of Comparative Example 2, though pain and allergic reaction were observed. The compositions of Examples 2, 3, 4 containing a local anesthetic and an antihistamine were shown to have remarkably reduced allergic redness, swelling, itching and pain compared with Example 1 or Comparative Example 2.

These effects are thought to result from the use of a local anesthetic and an antihistamine as well as the low dose hyaluronidase.

Further, in Example 3, some patients developed slight dimpling and sagging as a result of fat removal by the lipolysis stimulator, which were limited to highly obese patients and were recovered within a short period.

In Example 4, the inclusion of a collagen production stimulator allowed the rapid recovery of skin resilience, with no occurrence of dimpling or sagging.

Taken all together, the above effects are thought to result from the minimized unit dose of hyaluronidase, which allows administration of the injection composition over a wide area leading to even removal of fat, and the enhanced skin resilience due to the collagen production stimulator.

Hyaluronidase is an effective substance for topical fat reduction that has no particular side effects. It is known to have an efficacy nearly comparable to other conventional drugs and show few adverse interactions with other drugs. Thus, it is expected that hyaluronidase may maximize the therapeutic effect on obesity through combined administration with other drugs.

However, there have been many cases where treatment was discontinued or allergy drugs had to be administered due to side effects of the injection such as pain in injection sites or itching and swelling from allergic side effects. The present invention has been devised to provide an injection composition that can prevent the problem that the treatment must be discontinued due to such side effects despite being an effective and safe treatment for obesity, and remove fat over a wide area with a minimal dose.

It is to be understood that the above detailed description and working examples are provided by way of illustration only and are not to be taken by way of limitation.

Accordingly, a person of ordinary skill in the art would readily understand that various modifications and equivalents may be made without departing from the scope of the present invention.

Thus, the scope of protection for the present invention will be determined by the appended claims and equivalents thereof.

What is claimed is:

1. An injectable composition for local fat reduction comprising the following components: 300 IU to 600 IU of hyaluronidase and, based on the weight of the total composition, 0.08 to 0.4% by weight of lidocaine as a local anesthetic, 0.01 to 0.02% by weight of Peniramine as an antihistamine, 0.01 to 4.0% by weight of L-carnitine as a lipolysis stimulator, and 0.1 to 2.0% by weight of vitamin C as collagen stimulator, with the remainder being saline solution, wherein said components of the composition are present in a single dose injection of the injectable composition.

2. A process for local fat reduction comprising injecting single dose injection compositions at a unit volume of 0.5 to 2 cc with an interval between injection points of 0.5 to 1.5 cm, wherein the single dose injection composition comprises 300 IU to 600 IU of hyaluronidase and, based on the weight of the total composition, 0.08 to 0.4% by weight of lidocaine as a local anesthetic, 0.01 to 0.02% by weight of Peniramine as an antihistamine, 0.01 to 4.0% by weight of L-carnitine as a lipolysis stimulator, and 0.1 to 2.0% by weight of vitamin C as collagen stimulator, with the remainder being saline solution.

\* \* \* \* \*